United States Patent [19]

Inomata et al.

[11] Patent Number: 5,116,928

[45] Date of Patent: May 26, 1992

[54] PROCESS FOR PREPARING A FLUOROORGANOPOLYSILOXANE

[75] Inventors: Hiroshi Inomata, Takasaki, Japan; Yasuo Tarumi, Iowa City, Iowa

[73] Assignee: Shin-Etsu Chemical Co., Ltd., Tokyo, Japan

[21] Appl. No.: 481,240

[22] Filed: Feb. 20, 1990

[30] Foreign Application Priority Data

Feb. 21, 1989 [JP] Japan ................................ 1-40961

[51] Int. Cl.$^5$ ............................................... C08G 77/06
[52] U.S. Cl. ........................................ 528/18; 528/12; 528/21; 528/23; 528/37; 528/42
[58] Field of Search ................. 528/37, 42, 21, 23, 528/12, 18

[56] References Cited

U.S. PATENT DOCUMENTS

| | | | |
|---|---|---|---|
| 4,625,011 | 11/1986 | Kosal et al. | 528/37 |
| 4,814,418 | 3/1989 | Miyake et al. | 528/42 |

FOREIGN PATENT DOCUMENTS

| | | |
|---|---|---|
| 0252652 | 1/1988 | European Pat. Off. . |
| 0255957 | 2/1988 | European Pat. Off. . |
| 0311262 | 4/1989 | European Pat. Off. . |
| 2469422 | 5/1981 | France . |
| 2065153 | 6/1981 | United Kingdom . |

*Primary Examiner*—Melvyn I. Marquis
*Attorney, Agent, or Firm*—Oblon, Spivak, McClelland, Maier & Neustadt

[57] ABSTRACT

A process for preparing a fluoroorganopolysiloxane having a fluorine-containing organic group represented by the following formula:

$$F-(-C_gF_{2g}O-)_d-C_hF_{2h}CH_2-$$

where d represents an integer of from 1 to 5, g represents an integer of from 1 to 3, and h is 1 or 2, comprising the steps of:

polymerizing a monomer comprising a fluorine-containing cyclotrisiloxane having the following formula (II):

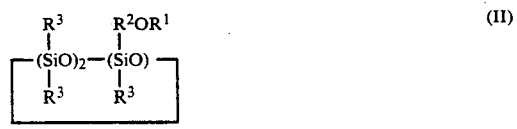

wherein $R^1$ represents the above fluorine-containing organic group, $R^2$ is a fluorine-free hydrocarbon group, and $R^3$ is a fluorine-free divalent hydrocarbon group, in the presence of an acidic catalyst or a basic catalyst, and in the presence of a water at a temperature of not higher than 80° C., and neutralizing the resulting polymerization product. This process can produce the above polymer containing little low molecular weight compounds and having a desired polymerization degree in a good yield.

7 Claims, 6 Drawing Sheets

Elution time

Elution time →

PROCESS FOR PREPARING A FLUOROORGANOPOLYSILOXANE

BACKGROUND OF INVENTION

1. Field of the Invention

The present invention relates to a novel process for preparing a fluoroorganopolysiloxane.

2. Description of the Prior art

Organopolysiloxanes have low surface tension and low refractive indexes, and are excellent in properties such as heat resistance, cold resistance, electrical insulation properties, water repellency, release properties, defoaming properties and chemical resistance; hence they are nowadays used in extensive industries. However, the recent progress of technology requires development of organopolysiloxanes excellent in various properties capable of satisfying high level of requirements. In attempt to satisfy, the requirements, for example, organopolysiloxanes having a fluorine-containing organic group were proposed.

The present inventors intended to produce an organopolysiloxane having a perfluoroalkylether group as the fluorine-containing group. Heretofore, as a conventional process of preparing an organopolysiloxane, there is known a process in which an organotrisiloxane having a desired pendant organic group is polymerized in the presence of such a catalyst as silanolates of alkali, e.g., Li, Na, K and Cs at 100° to 180° C. However, if this process is applied to an organotrisiloxane having said perfluoroalkylether group, polymerization proceeds with difficulty, and depolymerization also occurs to produce a considerable amount of low molecular weight compounds; hence it is impossible to produce a polymer with an intended polymerization degree in a good yield.

SUMMARY OF THE INVENTION

Accordingly, an object of the present invention is to provide a novel process for preparing a fluoroorganopolysiloxane having a perfluoroalkylether group, containing a small amount of low molecular weight compounds and having a desired polymerization degree.

Thus, the present invention provides a novel process for preparing fluoroorganopolysiloxane having the following general formula (I):

wherein $R^1$ represents a fluorine-containing organic group represented by the following formula:

$$F-(-C_gF_{2g}O-)_d-C_hF_{2h}CH_2-$$

where d represents an integer of from 1 to 5, g represents an integer of from 1 to 3, and h is 1 or 2,
$R^2$ represents a divalent substituted or unsubstituted hydrocarbon group having 3 to 10 carbon atoms and containing no fluorine atom, $R^3$ represents a substituted or unsubstituted hydrocarbon group containing 1 to 10 carbon atoms and containing no fluorine atom, $R^4$ has the same meaning as $R^3$ or represents a hydrogen atom or a group having the formula:

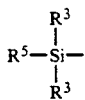

where $R^3$ is as defined above, $R^5$ has the same meaning as $R^3$ or represents a group having the formula: $-R^2OR^1$ where $R^1$ and $R^2$ are as defined above,
m is an integer of at least 2, and typically an integer of from 10 to 2,500, and n is an integer of not less than 1, and typically an integer of from 10 to 2,500, provided $m \geq 2n$,
said process comprising the steps of:
polymerizing a fluorine-containing cyclotrisiloxane having the following formula (II):

wherein $R^1$, $R^2$ and $R^3$ are as defined above, or a mixture of said fluorine-containing cyclosiloxane of the formula (II) and a cyclosiloxane having the following formula (III):

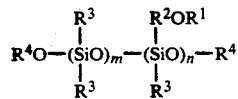

wherein $R^3$ is as defined above, in the presence of an acidic catalyst or a basic catalyst, and in the presence of water at a temperature of not higher than 80° C., and
neutralizing the resulting polymerization product.

According to the process of the present invention, it is possible to produce a fluoroorganopolysiloxane having a perfluoroalkylether group which contains a small amount of low molecular weight compounds and has an intended polymerization degree. This fluoroorganopolysiloxane is expected to satisfy some of recent requirements to raw materials for high-level functional materials.

DETAILED DESCRIPTION OF PREFERRED EMBODIMENTS

Fluoroorganopolysiloxane

Figure 1:
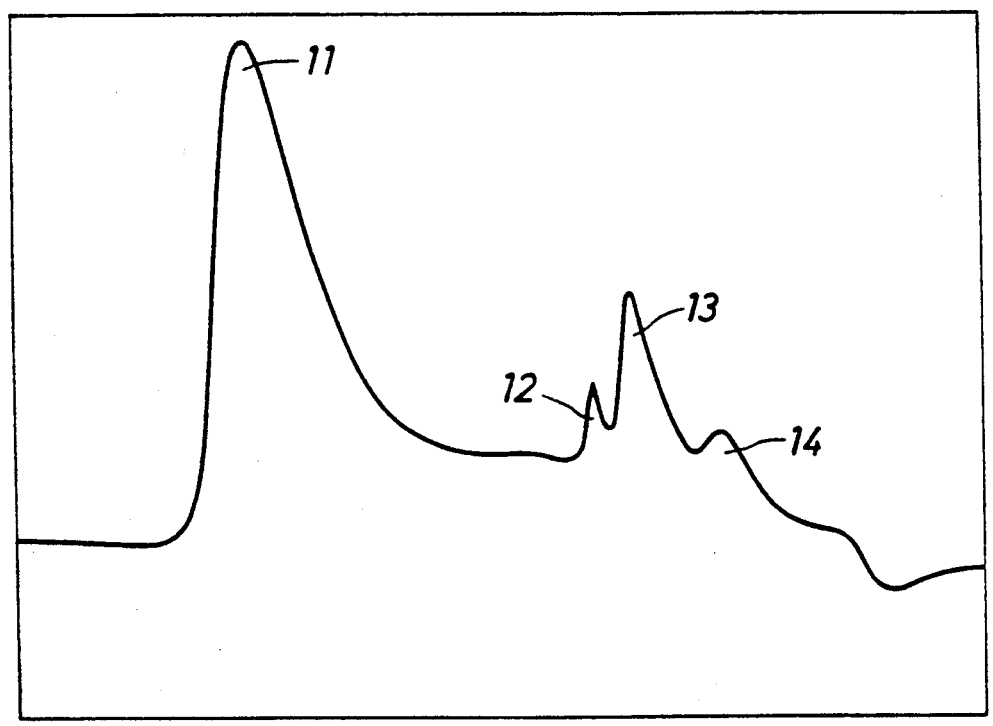
FIGS. 1, 2 and 3 show the GPC chart, $^1$H-NMR spectrum, and IR absorption spectrum, respectively, of the fluoroorganopolysiloxane obtained in Example 1.

In the general formula (I) of the fluoroorganopolysiloxane of the present invention, $R^1$ is a fluorine-containing organic group containing the perfluoroalkylether group having the following formula:

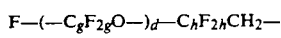

where g represents an integer of from 1 to 3, d represents an integer of from 1 to 5, and h is 1 or 2. Typically, $R^1$ has normally from 3 to 18 carbon atoms, and more typically has from 6 to 15 carbon atoms. The perfluoroalkylether group having too small a number of carbon atoms may impair the properties of the present polymer, such as release properties, low surface energy, etc. The fluorine-containing organic group includes, for example, the groups having the following formulas:

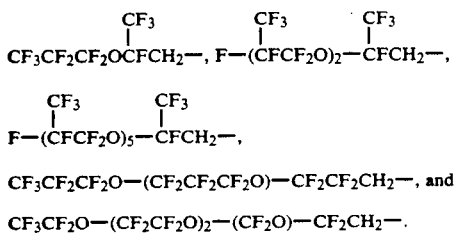

$CF_3CF_2CF_2O-(CF_2CF_2CF_2O)-CF_2CF_2CH_2-$, and $CF_3CF_2O-(CF_2CF_2O)_2-(CF_2O)-CF_2CH_2-$.

$R^2$ is a divalent substituted or unsubstituted hydrocarbon group having from 3 to 10 carbon atoms, and it includes, for example, alkylene groups such as a trimethylene group, a propylene group, and a 2-methyltrimethylene group; and alkylene groups substituted partly by a phenylene radical, such as

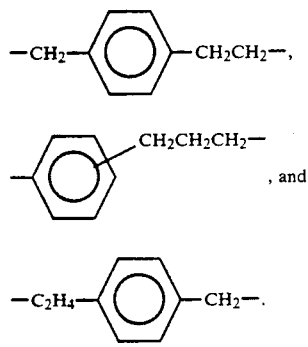

$R^3$ is a substituted or unsubstituted hydrocarbon group having from 1 to 10 carbon atoms and containing no fluorine atom. It includes, for example, alkyl groups such as a methyl group, an ethyl group, and a propyl group; aliphatic unsaturated hydrocarbon groups such as a vinyl group, an allyl group, and hexenyl group; aromatic hydrocarbon groups such as a phenyl group, a tolyl group, and a xylyl group; and corresponding substituted hydrocarbon groups having a substituent such as a halogen atom, cyano group, alkoxyl group, acryloyloxy group, methacryloyloxy group, and silyl group, including, e.g., a chloroethyl group, chloropropyl group, cyanoethyl group, and methoxyethyl group, $-C_3H_6OCO-C(-R^6)=CH_2$, $-C_2H_4Si(OR^7)_3$, $-C_2H_4Si(OR^7)_3$, $-CH_2CH(-R^6)-COOC_3H_6Si(OR^7)_3$,

wherein $R^7$ is a $C_1$ to $C_5$ alkyl group, or a $C_2$ to $C_5$ alkoxyalkyl group or alkenyl group, and $R^6$ is a hydrogen atom or a methyl group.

The symbol a is a number of from 0.001 to 0.34, b is a number of from 1.64 to 2.34, c is a number of from 0 to 0.67, and a+b+c ranges from 1.90 to 2.67.

There is no limitation on the amount of the aliphatic unsaturated hydrocarbon groups contained as an $R^3$ in the molecule of the fluoroorganopolysiloxane of the present invention. In the case the fluoroorganopolysiloxane of the present invention is used as an ingredient of a fluorosilicone rubber, the amount of the aliphatic unsaturated groups is suitably adjusted according to purposes, and normally ranges from 0.2 to 30 mol % of all the pendant groups bonded to silicon atoms. In the case it is used as a silicone gel, it may contain less than two aliphatic unsaturated groups on average in the molecule, because it is required that the molar ratio of silicon-bonded hydrogen atoms of an organohydrogenpolysiloxane used in combination to the silicon-bonded aliphatic unsaturated groups in the fluoroorganopolysiloxane of the invention ranges from 1 to 1.5.

Typical examples of the fluoroorganopolysiloxane represented by the above general formula (I) of the present invention include:

(1) compounds represented by the general formula (II) wherein $R^4$ at the both ends of the molecule is a triorganosilyl group having the formula:

where $R^3$ and $R^5$ are as defined above, for example, the compounds of the following formulas:

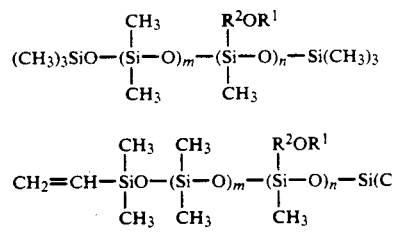

wherein $R^1$, $R^2$, m and n are as defined above; and (2) compounds represented by the general formula (II) wherein m+n ranges from 3 to 2,000, and the ends of the molecule are terminated by a silanol group.

The viscosity of the fluoroorganopolysiloxane produced by the present process is not prticularly limited. However, it normally has a viscosity of not more than $1 \times 10^6$ cP at 25° C.

Starting Materials

The fluorine-containing cyclotrisiloxane of the formula (II) includes, for example, the compounds represented by the following formulas:

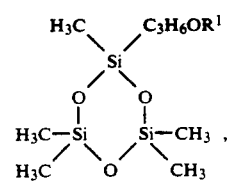

-continued

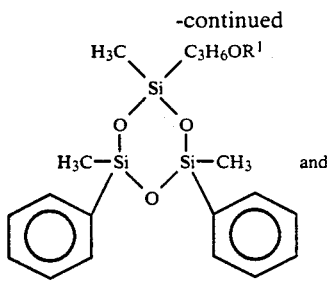
and

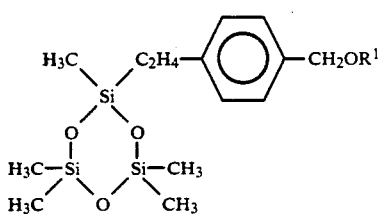

wherein R¹ is as defined above.

The cyclotrisiloxane of the formula (III) includes, for example, the compounds represented by the following formulas:

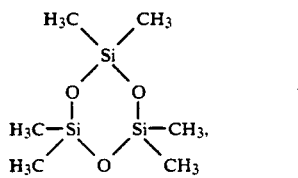,

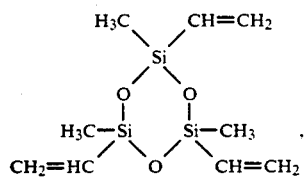,

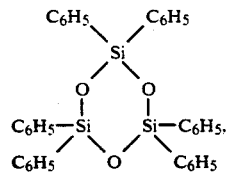,

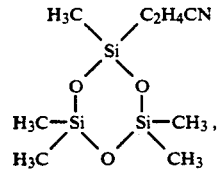,

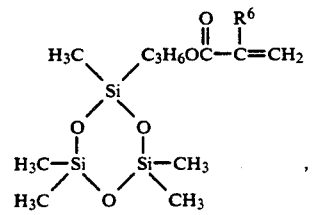,

-continued

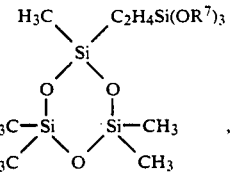,

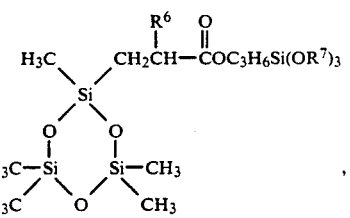, and

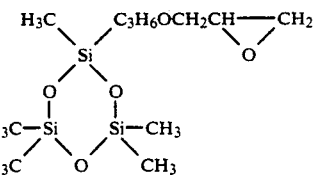

wherein $R^6$ and $R^7$ are as defined above.

In the case where a mixture of the fluorine-containing cyclotrisiloxane of said formula (II) and the cyclotrisiloxane of the formula (III) is used in the preparation of the fluoroorganopolysiloxane of the present invention, the mixing ratio of the fluorine-containing cyclotrisiloxane of said formula (II) to the cyclotrisiloxane of said formula (III) is decided suitably according to an intended fluoroorganopolysiloxane of the formula (I), and it normally ranges from 99.9/0.1 to 0.1/99.9, by weight.

The fluorine-containing cyclotrisiloxane of the above formula (II) can be prepared, for example, by the process using a perfluoroalkylene oxide, exemplified below, as a starting material.

First, as shown in the equation (a) below, a perfluoroalkylene oxide having the formula (V) is polymerized in the presence of a catalyst in a non-protonic polar solvent to produce an acid fluoride having the formula (VI). (See H. S. Eleuterio, J. Macromol Sci-Chem., A6(6), 1027 (1979); U.S. Pat. No. 3,250,808; and Japanese pre-examination patent publication (KOKAI) No. 195345/1987).

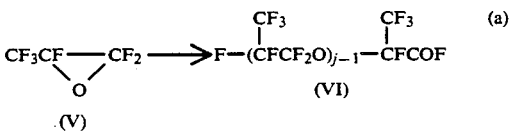

wherein j is an integer of from 2 to 6.

The non-protonic solvent used in this reaction includes, for example, tetraglyme. The catalyst includes, for example, cesium fluoride CsF, potassium fluoride, and the like.

Subsequently, the acid fluoride of the formula (VI) obtained is reduced with a reducing agent such as, e.g., LiAlH₄ and NaBH₄, followed by hydrolysis to produce a perfluoroalkyl polyether alcohol represented by the following formula (VII):

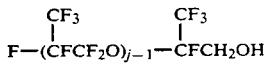 (VII)

(See U.S. Pat. No. 3,293,306).

The perfluoroalkylpolyetheralcohol of the formula (VII) is reacted with a halogenated alkene, e.g., allyl bromide to produce, for example, an ether compound having a vinyl group at its end represented by the following formula (VIII):

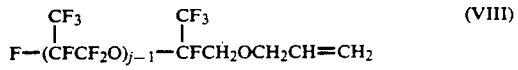 (VIII)

(see the specification of Japanese Patent Publication (KOKOKU) No. 253044/1988). In order to allow this reaction to proceed smoothly, for example, a basic substance such as sodium hydroxide, or a phase-transfer catalyst such as tetrabutylammonium hydrogen-sulfuric acid may be used.

The ether compound of the formula (VIII) and methyldichlorosilane are subjected to addition reaction in the presence of a platinum catalyst according to the following equation (b) to produce a silane compound of the formula (IX). (See the specification of Japanese Patent Publication (KOKOKU) No. 255288/1988).

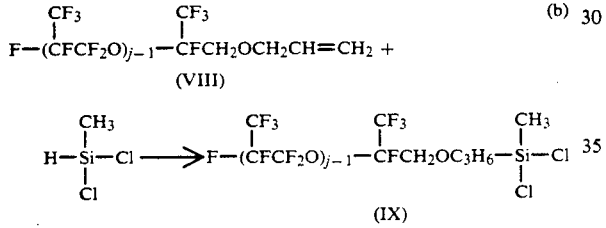 (b)

Subsequently, the silane compound of the formula (IX) and tetramethyldisiloxane diol are subjected to dehydrochlorination to produce a fluorine-containing cyclotrisiloxane having the formula (IIa):

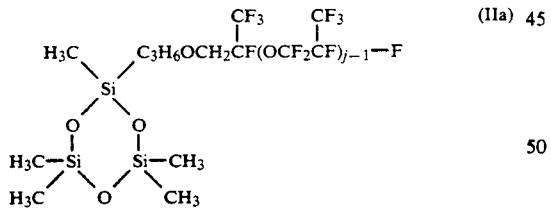 (IIa)

(See the specification of Japanese Patent Application No. 71887/1989). The dehydrochlorination agent which may be used includes, for example, tertiary amines such as triethylamine and active hydrogen-free cyclic amines such as pyridine.

In the foregoing description, the preparation of the fluorine-containing cyclotrisiloxane of the formula (II) are described based on a particular example. However, selection of a starting material corresponding to an intended fluorine-containing cyclotrisiloxane of the formula (II) makes it possible to produce a variety of fluorine-containing cyclotrisiloxanes of the formula (II). Particularly, change of the starting perfluoroalkylene oxide and the preparation process can provide an acid fluoride having a structure differing from that of the above formula (VI). (See Japanese Patent Publication No. 11164/1971). From the acid fluorides with a different structure, fluoroorganopolysiloxanes various perfluoroalkylether groups can be prepared. In the case of the preparation process described above, use of a mixed starting material containing various perfluoroalkylene oxides can bring about a mixture of various fluorine-containing cyclotrisiloxanes having different perfluoroalkylether groups.

Polymerization step

The fluorine-containing cyclotrisiloxane of the formula (II) obtained as described above, or a mixture of it with the cyclotrisiloxane of the formula (III) is polymerized in the presence of a basic catalyst or an acidic catalyst and in the presence of water to produce the fluoroorganopolysiloxane of the present invention.

Preferably, the basic catalyst which can be used includes, for example, quaternary phosphonium hydroxides, quaternary ammonium hydroxides, and silanolates thereof. The quaternary phosphonium hydroxides include, for example, the compounds having the formulas:

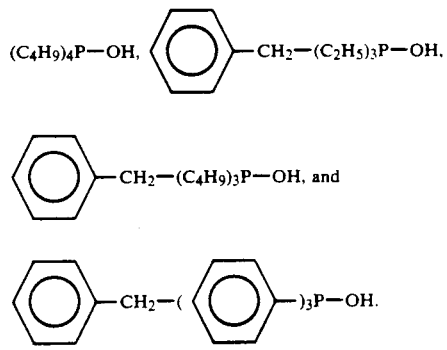

The quaternary ammonium hydroxides include, for example, the compounds having the formulas:

$(CH_3)_4N-OH$, $(C_4H_9)_4N-OH$, and

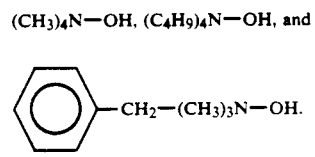

Silanolation of the quaternary phosphonium hydroxide or the quaternary ammonium hydroxide can be performed, for example, by heating an aqueous solution of it with octamethycyclotetrasiloxane at from 50° to 60° C. under stirring, with water being distilled under reduced pressure.

The acidic catalyst preferably includes, for example, $ClSO_3H$, $CF_3SO_3H$, $FSO_3H$, $H_2SO_4$, and $PNCl_2$.

The amount of the catalyst is not particularly limited. Normally, the catalyst is preferably used in an amount such that the molar ratio of all the Si in the fluorine-containing cyclotrisiloxane of said formula (III) and the cyclotrisiloxane of the formula (IV) to the catalyst molecule may range from about 500 to 3,000. If the catalyst is used in too large an amount, neutralization treatment after the polymerization become harder, and salts formed by the neutralization may exert bad influence upon the properties of the resulting fluoroorganopolysiloxane.

Polymerization is normally carried out at 80° C. or lower. In the case an acidic catalyst is used, preferably at from −10° to 60° C., and more preferably at from 0° to 30° C. In the case a basic catalyst is used, at from 10° to 80° C. and more preferably at from 20° to 60° C. At too high a temperature, formation of low molecular weight cyclic compounds may be promoted by equilibration reaction.

Polymerization time can be set to within a time of for from several minutes to several hours as required. Preferably, the polymerization time is set to from 30 minutes to several hours by regulating the catalyst amount and/or polymerization temperature so that a fluoroorganopolysiloxane with a desired polymerization degree may be prepared.

As a solvent for polymerization, for example, nonprotonic solvents such as tetrahydrofrun, dioxane, diglyme, tetraglyme, dimethylformamide, and acetonitrile, or inert solvents such as frons may be used.

NEUTRALIZATION STEP

In the neutralization step, a neutralizing agent to be used is required to be selected according to the catalyst used in the polymerization step and the intended terminal structure of an end fluoroorganopolysiloxane.

In the first embodiment of the present process, said polymerization is carried out in the presence of an acidic catalyst and water, and the resulting polymerization product is neutralized with a basic substance, thereby said fluoroorganopolysiloxane is produced as one terminated with the group having the formula:

where $R^3$ is as defined above. The basic substance used includes, for example, ammonia and amine compounds, which are preferably used as an aqueous solution. The amine compound to be used is preferably one which can be distilled away, including, for example, lower alkylamines such as dimethylamine, propylamine, and ammonium carbonate. In this case, normally, the basic substance for neutralization is preferably used in an amount such that the nitrogen atoms contained in the basic substance is from 1 to 5 times by equivalent weight the acidic catalyst used. After polymerization, formed salts and the excess basic substance are preferably removed.

According to the second embodiment of the present process, said polymerization is carried out in the presence of a basic catalyst and water, and the resulting polymerization catalyst is neutralized with an acidic substance, thereby said fluoroorganopolysiloxane is produced as one terminated with the group having the formula:

where $R^3$ is as defined above. The acidic substance used includes, for example, mineral acids such as dilute sulfuric acid, dilute hydrochloric acid and phosphoric acid. Normally, the acidic substance is preferably used in an amount 0.8 to 3 times by equivalent weight that of the basic catalyst used. After the neutralization treatment, salts and the excess acidic substance are preferably removed.

According to the third embodiment of the present process, said polymerization is carried out in the presence of a basic catalyst and water, and the resulting polymerization product is neutralized with a halosilane compound the having formula (X):

$$R^5(R^3)_2SiX \qquad (X)$$

wherein $R^3$ and $R^5$ are as defined above, and X represents a halogen atom, and a disilazane compound having the formula (XI):

$$[R^5(R^3)_2Si]_2NH \qquad (XI)$$

wherein $R^3$ and $R^5$ are as defined above, in combination, thereby said fluoroorganopolysiloxane is produce as one terminated with the group having the formula:

$$R^5(R^3)_2Si-$$

wherein $R^3$ and $R^5$ are as defined above.

The halosilane of said formula (X) used in the neutralization, which serves as a neutralizing agent, includes, for example, trialkylhalosilanes represented by the formulas:

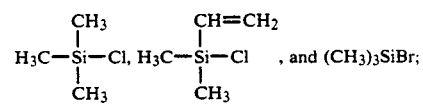

halosilanes having a vinyl group, phenyl group, etc. such as $CH_2=CH(CH_3)_2SiI$, $(CH_2=CH)_3SiCl$, and $CH_2=CHSi(C_6H_5)(CH_3)Cl$.

The disilazane compound of said formula (XI) serves to capture hydrochloric acid which may be by-produced by hydrolysis of said halosilane compound and thereby to control depolymerization. It includes, for example, hexacarbyldisilazanes such as the compounds represented by the formulas:

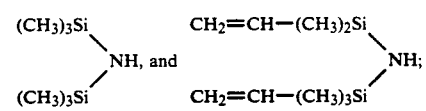

and silazanes having a fluorine-containing organic group, such as the compounds represented by the formulas:

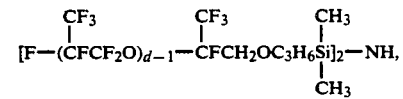

wherein d is as defined above.

The halosilane compound is normally used in an amount such that the molar ratio of it to the catalyst used for polymerization may range from about 0.8 to about 3.0. The disilazane compound is normally used in an amount such that the molar ratio of it to the catalyst used for the polymerization may range from about 0.5 to about 10. The use of the halosilane compound or the disilazane compound in too large an amount may make the resulting fluoroorganopolysiloxane unstable.

Where the fluoroorganopolysiloxane is made terminated with a triorganosilyl group according to the third embodiment, a vinyl group or other functional group can be introduced as a part of the organic groups possessed by the terminal triorganosilyl group.

OTHER CONDITIONS

In the preparation of the fluoroorganopolysiloxane of the present invention, in order to make easier the stirring during polymerization, neutralization, the dissolving or dispersing of a neutralizing agent, or removal by filtration of salts formed by neutralization, an inert solvent may be used as required. Such inert solvents include, for example, fluorine solvents such as from 113, and m-xylene hexafluoride, chlorine solvents such as methylene chloride and trichloroethane.

USES

The fluoroorganopolysiloxane of the present invention has a low surface tension and refractive index, and is excellent in properties such as cold resistance and oil resistance. Hence, it is expected to be also used for release agents, fiber modifiers, liquid rubbers, and heat-cure rubbers.

EXAMPLES

The present invention will be described in detail by way of working examples and comparative examples below. In the description below, the fluorine-containing cyclotrisiloxane having the formula (IIb):

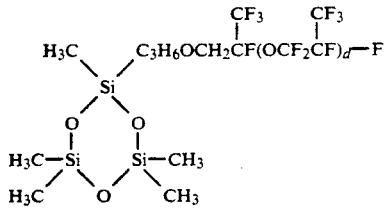

which is an example of the fluorine-containing cyclotrisiloxane of said formula (II) is abbreviated to $D_2{}^d$, where d is as defined above, i.e., an integer of from 1 to 5. The viscosities were measured at 25° C.

EXAMPLE 1

In a four-necked flask with a volume of 200 ml, 50.0 g of $D_2F^1$(purity: 99.4%) was charged and then heated to 40° C. Then, 479 mg of a solution containing 10% water in 1,4-dioxane was added thereto, and the contents in the flask was mixed under stirring. Thereafter, 0.102 g of 10% $CF_3SO_3H$ solution in m-xylene hexafluoride was added thereto, followed by polymerization at 40° C. One minute later, increase in viscosity of the reaction mixture was observed. Another 120 minutes later, 50 g of from 113 and a 2.8% aqueous ammonia was added and a heater was taken away from the flask, and neutralization was carried out under stirring. Then, 0.5 g of activated charcoal was added, and adsorption treatment was carried out under stirring for 60 minutes. The reaction mixture thus treated was filtered to give a transparent filtrate. The filtrate was subjected to stripping at 110° C. under a reduced pressure of 6 mmHg for 30 minutes to give an organopolsiloxane terminated with silanol groups having a viscosity of 3,600 cP, a refractive index of 1.3636, a specific gravity of 1.29 and a terminal silanol group content of 0.008 mol/100 g. The organopolysiloxane was analyzed by GPC, and the result shown in FIG. 1 was obtained, in which the peak 11 due to high molecular weight compounds, and the peaks 12, 13 and 14 (total area: ca. 23%) due to low molecular weight compounds appeared. The results from this analysis showed that the organopolysiloxane obtained contained the high molecular weight compounds as well as about 23% of low molecular weight compounds.

Figure 2:
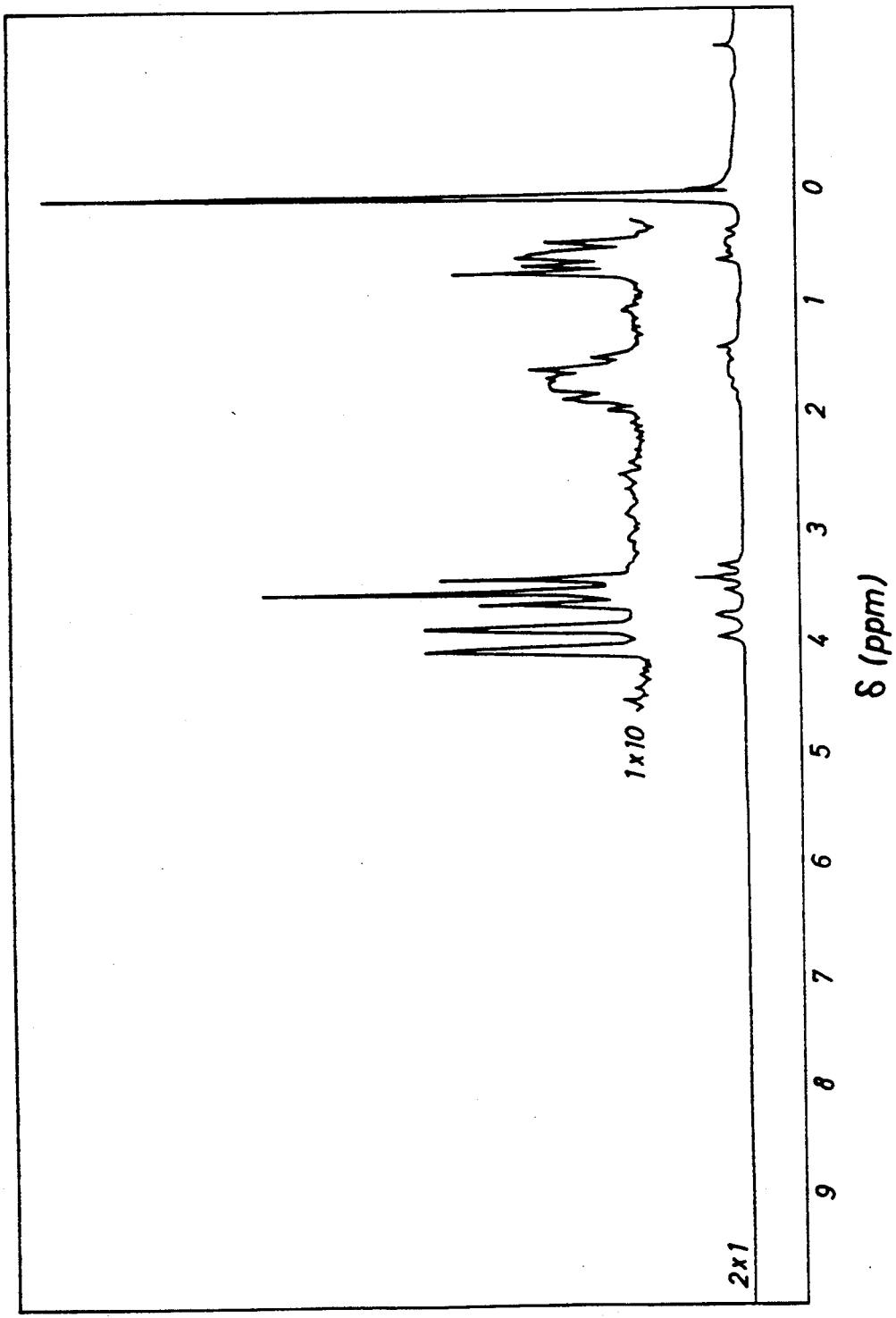
Figure 3:
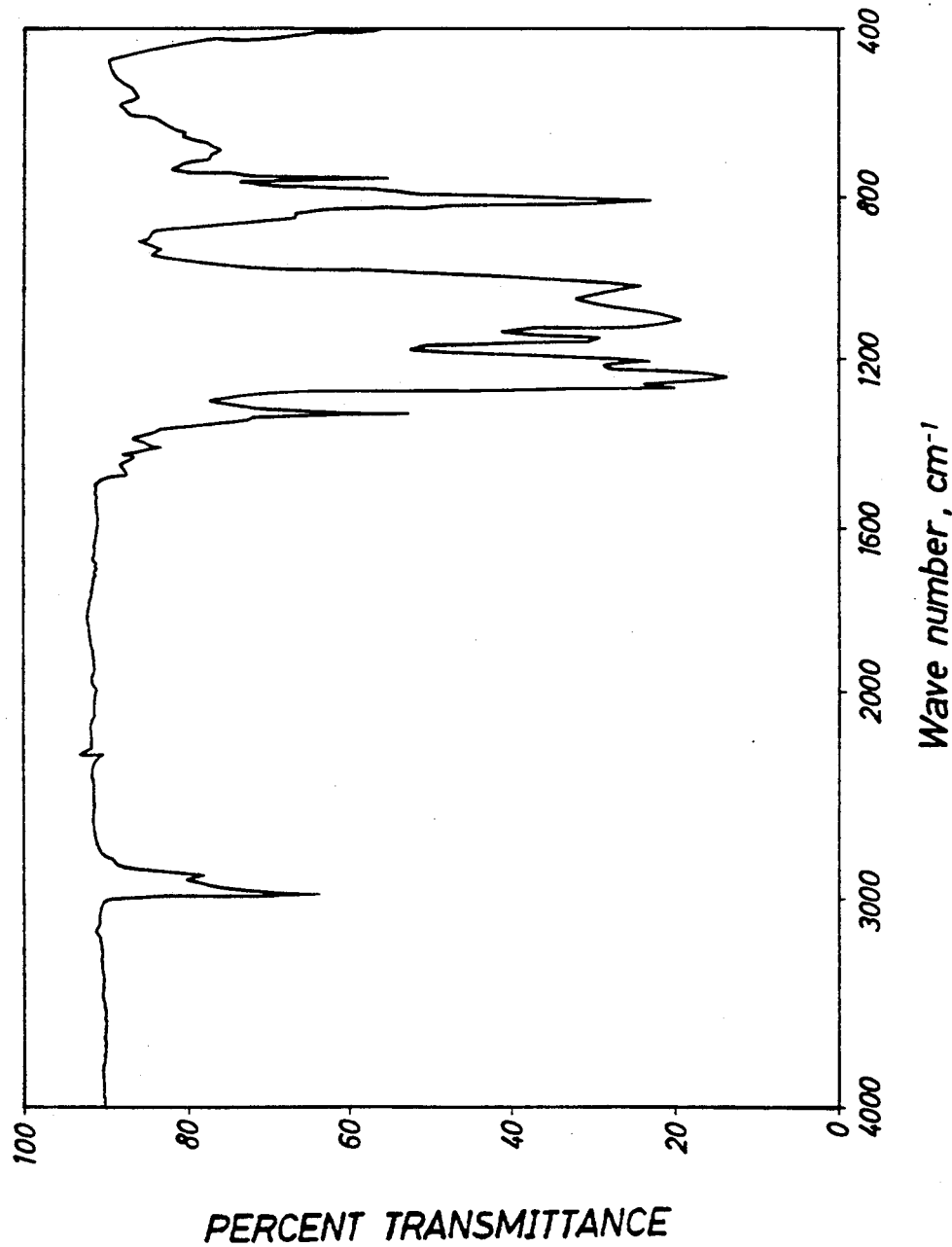

FIGS. 2 and 3 show an NMR spectrum and an IR absorption spectrum, respectively, of the above polysiloxane.

EXAMPLE 2

In a four-necked flask, 56.4 g of $D_2F^1$ was charged, and then the inside was replaced with a dry nitrogen gas by passing a stream thereof through the flask at 40° C. for 30 minutes. Then, 2.7 g of 1% water solution in dioxane was added, and the contents in the flask was uniformly mixed. Subsequently, 0.33 g of a catalyst consisting of dimethylsilanolate of $(C_4H_9)_4POH$ ($(C_4H_9)_4POH$ content: 10%) (hereinafter, referred to as "TBPH catalyst") was added thereto so that the molar ratio of Si/P in the reaction system might become 2,500. Thereafter, polymerization was initiated at 40° C. under a stream of nitrogen. The reaction mixture was transparent, and reaction proceeded at a relatively slow rate. After 2 hours, 3.6 g of 0.49% sulfuric acid solution in water/dioxane (weight ratio: 1/1) was added, and neutralization was carried out for 1 hour. After the heater was taken away, 0.8 g of a 0.7% aqueous ammonia was added to the reaction mixture thus treated to neutralize the excess sulfuric acid therein. The reaction mixture was then diluted with 70 g of fron 113, 10 g of $Na_2SO_4$ and 0.56 g of active charcoal were added thereto, and treatments of dehydration and adsorption were carried out for 1 hour, followed by filtration. The resulting transparent filtrate was subjected to stripping by heating at 80° C. under a reduced pressure of 700 mmHg. Finally, stripping was carried out at 80° C. under a pressure of 5 mmHg with a nitrogen gas being bubbled therethrough, resulting in 51.0 g of a colorless transparent fluoroorganopolysiloxane terminated with silanol groups. Incidentally, no distillation of siloxanes was observed when the stripping was carried out.

The viscosity, specific gravity, refractive index, and silanol group content of the fluoroorganopolysiloxane obtained were measured to be 6,500 cP, 1,29, 1.3643, and 0.008 mol/100 g, respectively. The viscosity after aging at 70° C. for 24 hours was measured to be 7,000 cP, indicating that the polymer had a relatively good stability.

Figure 4:
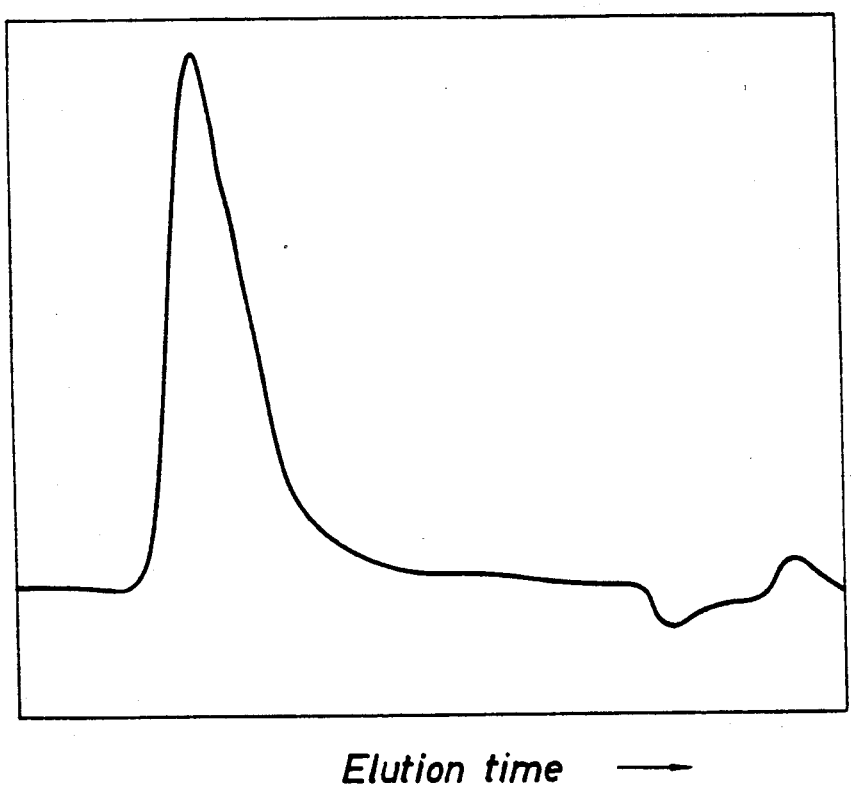
FIGS. 4, 5 and 6 show the GPC chart, IR absorption spectrum, and $^1$H-NMR spectrum, respectively, of the fluoroorganopolysiloxane obtained in Example 2.

The fluoroorganopolysiloxane was analyzed by GPC in the same manner as in Example 1. As shown in FIG. 4, it was found that the polymer hardly contained low molecular weight compounds.

Further, the IR absorption spectrum and $^1H$-NMR spectrum were measured. The results obtained are as shown below.

IR Absorption Spectrum

Figure 5:
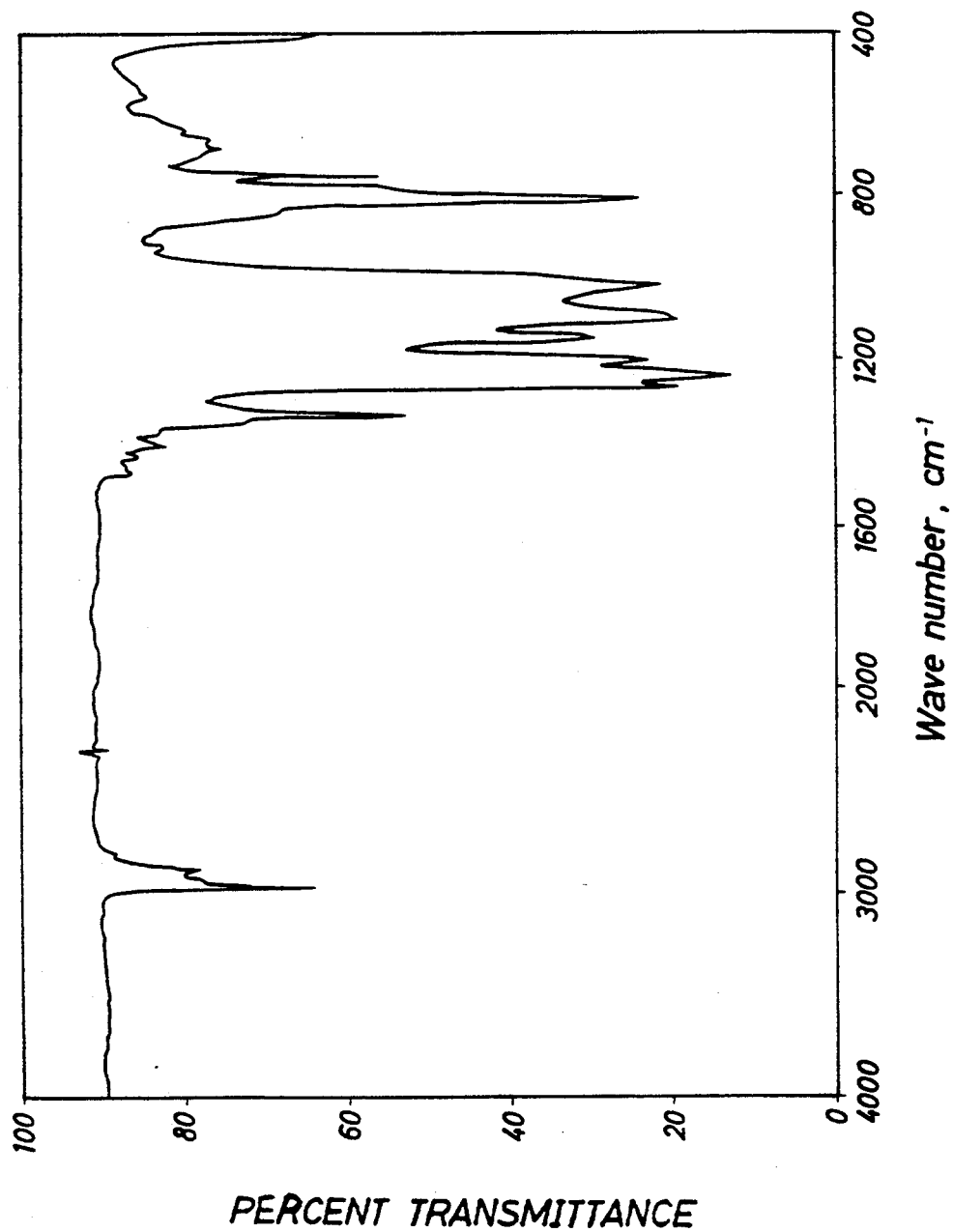

The spectrum is as shown in FIG. 5. Main characteristic absorption bands are as follows.

1,000 to 1,130 cm$^{-1}$ (Si-O-Si)
2,970, 1,260, 810 cm$^{-1}$ (Si-CH$_3$)

1,000 to 1,400 cm$^{-1}$ (C-F)

$^1$H-NMR

Figure 6:
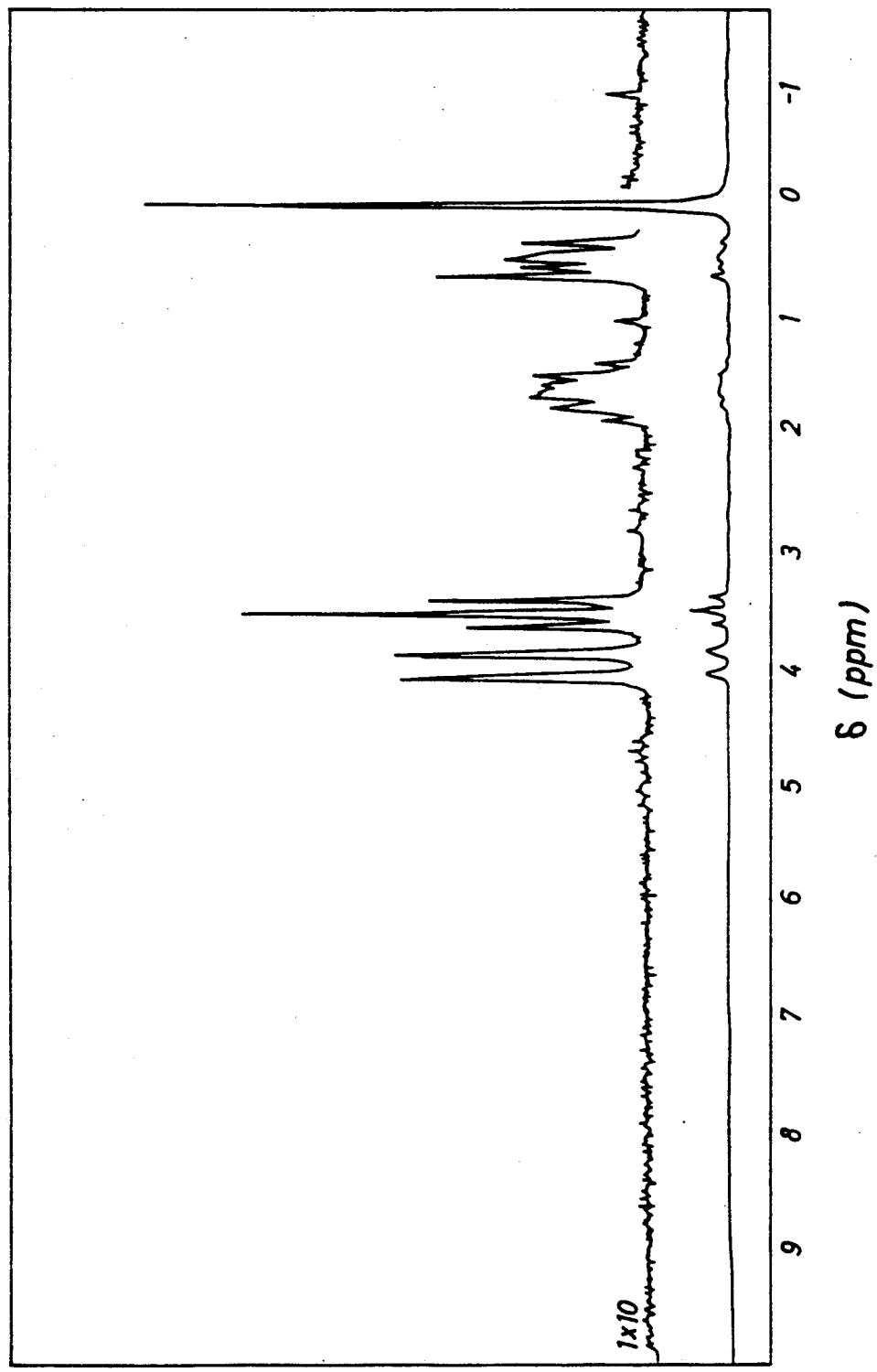

The spectrum shown in FIG. 6 was obtained (20% solution in fron 113; internal standard: Si—CH$_3$)

δ:

3.70–4.05 ppm (d, —CFC$\underline{H}_2$—, 2H)

3.29–3.60 ppm (t, —OC$\underline{H}_2$CH$_2$CH$_2$, 2H)

1.34–1.87 ppm (m, —CH$_2$C$\underline{H}_2$CH$_2$—, 2H)

0.29–0.67 ppm (m, —C$\underline{H}_2$—Si, 2H)

EXAMPLE 3

In a four-necked flask, 243.3 g of D$_2$F$^2$ (purity: 99.4%) was charged and polymerized, and the fluoroorganopolysiloxane obtained was subjected to the treatments of neutralization, dehydration and adsorption in the same manner as in Example 2, provided under the conditions described below.
Amount of 1% water solution in dioxane 9.0 g
Amount of TBPH catalyst 1.90 g
Polymerization temperature 40° C.
0.49% sulfuric acid solution in water/dioxane 8.26 g
2.8% aqueous ammonia 0.42 g
Na$_2$SO$_4$ for dehydration treatment 23 g
Active charcoal for adsorption treatment 3.6 g The fluoroorganopolysiloxane obtained was colorless and transparent. The viscosity, specific gravity and refractive index ($n_D^{25}$) were measured to be 13,000 cP, 1.38, and 1.3526, respectively. This fluoroorganopolysiloxane did not dissolve in tetrahydrofuran.

We claim:

1. A process for preparing a fluoroorganopolysiloxane having the following general formula (I):

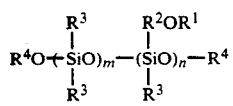
(I)

wherein R$^1$ represents a fluorine-containing organic group represented by the following formula:

F—(—C$_g$F$_{2g}$O—)$_d$—C$_h$F$_{2h}$CH$_2$— where d represents an integer of from 1 to 5, g represents an integer of from 1 to 3, and h is 1 or 2, R$^2$ represents a divalent substituted or unsubstituted hydrocarbon group having 3 to 10 carbon atoms and containing no fluorine atom, R$^3$ represents a substituted or unsubstituted hydrocarbon group containing 1 to 10 carbon atoms and containing no fluorine atom, R$^4$ has the same meaning as R$^3$ or represents a hydrogen atom or a group having the formula:

wherein R$^3$ is as defined above, R$^5$ has the same meaning as R$^3$ or represents a group having the formula: —R$^2$OR$^1$ wherein R$^1$ and R$^2$ are as defined above, m is an integer of at least 2, and n is an integer of not less than 1, provided m ≧ 2n, said process comprising the steps of:

polymerizing a fluorine-containing cyclotrisiloxane having the following formula (II):

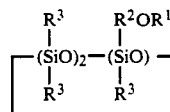
(II)

wherein R$^1$, R$^2$ and R$^3$ are as defined above, or a mixture of said fluorine-containing cyclosiloxane of the formula (II) and a cyclosiloxane having the following formula (III):

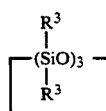
(III)

wherein R$^3$ is as defined above, in the presence of an acidic catalyst or a basic catalyst selected from the group consisting of quaternary phosphonium hydroxides, quaternary ammonium hydroxides, and silanolates thereof, and in the presence of water at a temperature of not higher than 80° C., and neutralizing the resulting polymerization product by adding a neutralizing agent.

2. The process of claim 1, wherein said polymerization is carried out in the presence of an acidic catalyst and water, and said neutralizing is carried out with a basic substance, thereby said fluoroorganopolysiloxane is produced as one terminated with the group having the formula:

where R$^3$ is as defined above.

3. The process of claim 1, wherein said polymerization is carried out in the presence of a basic catalyst and water, and said neutralizing is carried out with an acidic substance, thereby said fluoroorganopolysiloxane is produced as one terminated with the group having the formula:

where R$^3$ is as defined in claim 1.

4. The process of claim 1, wherein said polymerizing is carried out in the presence of a basic catalyst and water, and said neutralizing is carried out with a halosilane compound having the formula (X):

R$^5$(R$^3$)$_2$SiX   (X)

wherein R$^3$ and R$^5$ are as defined in claim 1, and X represents a halogen atom, and a disilazane compound having the formula (XI):

$$[R^5(R^3)_2Si]_2NH \quad \text{(XI)}$$

wherein $R^3$ and $R^5$ are as defined in claim 1, in combination, thereby said fluoroorganopolysiloxane is terminated with the group having the formula:

$$R^5(R^3)_2Si-$$

wherein $R^3$ and $R^5$ are as defined in claim 1.

5. The process of claim 1, wherein each of m and n is an integer of from 10 to 2,500.

6. The process of claim 1, wherein said basic catalyst is a quaternary phosphonium hydroxide or silanolate thereof.

7. The process of claim 4, wherein said basic catalyst is a quaternary phosphonium hydroxide or silanolate thereof.

* * * * *